(12) United States Patent
Kindermann et al.

(10) Patent No.: US 8,178,314 B2
(45) Date of Patent: May 15, 2012

(54) PYRIMIDINES REACTING WITH O6-ALKYLGUANINE-DNA ALKYLTRANSFERASE FUSION PROTEIN AND METHOD FOR DETECTING PROTEIN

(75) Inventors: Maik Kindermann, Frankfurt (DE); Markus Schwab, Lörrach (DE)

(73) Assignee: Covalys Biosciences AG, Witterswil (CH)

( * ) Notice: Subject to any disclaimer, the term of this patent is extended or adjusted under 35 U.S.C. 154(b) by 986 days.

(21) Appl. No.: 11/918,936

(22) PCT Filed: Apr. 25, 2006

(86) PCT No.: PCT/EP2006/061798
§ 371 (c)(1),
(2), (4) Date: Nov. 19, 2007

(87) PCT Pub. No.: WO2006/114409
PCT Pub. Date: Nov. 2, 2006

(65) Prior Publication Data
US 2009/0186373 A1  Jul. 23, 2009

(30) Foreign Application Priority Data
Apr. 27, 2005 (EP) .................................. 05103477

(51) Int. Cl.
*C12Q 1/48* (2006.01)
*C09B 29/52* (2006.01)
(52) U.S. Cl. .......................................... 435/15; 534/767
(58) Field of Classification Search .................. None
See application file for complete search history.

(56) References Cited

U.S. PATENT DOCUMENTS

| 5,753,668 A | 5/1998 | Moschel et al. |
| 5,958,932 A | 9/1999 | Moschel et al. |
| 6,096,724 A | 8/2000 | McMurry et al. |
| 2006/0024775 A1 | 2/2006 | Kindermann et al. |

FOREIGN PATENT DOCUMENTS

| WO | 2004/031405 | 4/1994 |
| WO | 96/04281 | 2/1996 |
| WO | 97/20843 | 6/1997 |
| WO | 02/083937 | 10/2002 |
| WO | 2005/085470 | 9/2005 |

OTHER PUBLICATIONS

Antje Keppler et al., "A General Method for the Covalent Labeling of Fusion Proteins with Small Molecules in Vivo", Nature Biotechnology, vol. 21., Jan. 2003, pp. 86-89.
International Search Report filed in International Application No. PCT/EP2006/061798 filed Apr. 25, 2006.

*Primary Examiner* — David Naff
(74) *Attorney, Agent, or Firm* — New England Biolabs, Inc; Harriet M. Strimpel

(57) ABSTRACT

The invention relates to pyrimidines suitable as substrates for $O^6$-alkylguanine-DNA alkyltransferases (AGT) of formula (I)

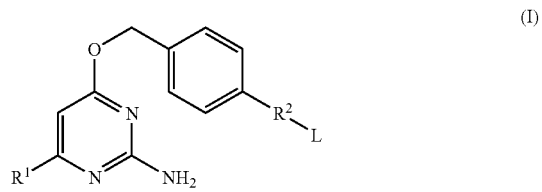

wherein $R^1$ is hydrogen, lower alkyl, halogen, cyano, trifluoromethyl or azido; $R^2$ is a linker; and L is a label or a plurality of same or different labels. The invention further relates to methods of transferring a label from pyrimidines of formula (I) to $O^6$-alkylguanine-DNA alkyltransferases (AGT) and AGT fusion proteins.

14 Claims, 6 Drawing Sheets

A

B

C

A

B

C

A

B

C

A

B

C

PYRIMIDINES REACTING WITH O6-ALKYLGUANINE-DNA ALKYLTRANSFERASE FUSION PROTEIN AND METHOD FOR DETECTING PROTEIN

This application is a U.S. national stage of International Application No. PCT/EP2006/061798 filed Apr. 25, 2006.

FIELD OF THE INVENTION

The present invention relates to methods of transferring a label from substrates to $O^6$-alkylguanine-DNA alkyltransferases (AGT) and $O^6$-alkylguanine-DNA alkyltransferase fusion proteins, and to pyrimidines suitable as substrates in such methods.

BACKGROUND OF THE INVENTION

The mutagenic and carcinogenic effects of electrophiles such as N-methyl-N-nitrosourea are mainly due to the $O^6$-alkylation of guanine in DNA. To protect themselves against DNA-alkylation, mammals and bacteria possess a protein, $O^6$-alkylguanine-DNA alkyltransferase (AGT) which repairs these lesions. AGT transfers the alkyl group from the position $O^6$ of alkylated guanine and guanine derivatives to the mercapto group of one of its own cysteines, resulting in an irreversibly alkylated AGT. The underlying mechanism is a nucleophilic reaction of the $S_N2$ type which explains why not only methyl groups, but also benzylic groups are easily transferred. As overexpression of AGT in tumour cells is the main reason for resistance to alkylating drugs such as procarbazine, dacarbazine, temozolomide and bis-2-chloroethyl-N-nitrosourea, inhibitors of AGT have been proposed for use as sensitisers in chemotherapy (Pegg et al., Prog Nucleic Acid Res Mol Biol 51:167-223, 1995). WO 97/20843 describes 4-heteroarylmethoxy-pyrimidines acting as AGT depleting compounds and their use for depleting AGT levels in tumor cells and thereby increasing responsiveness to alkylating anti-tumor drugs.

WO 02/083937 discloses a method for detecting and/or manipulating a protein of interest wherein the protein is fused to AGT and the AGT fusion protein contacted with an AGT substrate carrying a label, and the AGT fusion protein detected and optionally further manipulated using the label. Several AGT fusion proteins to be used, general structural principles of the AGT substrate and a broad variety of labels and methods to detect the label useful in the method are described.

WO 2004/031404 describes particular AGT fusion proteins to be used in the mentioned method for detecting and/or manipulating a protein of interest, labelled fusion proteins obtainable by this method, and the method using the particular AGT fusion proteins; and the related WO 2004/031405 discloses additional AGT substrates carrying a label particularly suitable in the mentioned method for detecting and/or manipulating a protein of interest, and the application of such particularly labelled substrates.

Unpublished PCT/EP2005/050899 describes AGT mutants suitable in the method. Related unpublished PCT/EP2005/050900 discloses further AGT substrates with a guanine (purine), azapurine or pyrimidine nucleus carrying a label particularly suitable in the mentioned method for detecting and/or manipulating a protein of interest, and the application of such particularly labelled substrates.

SUMMARY OF THE INVENTION

The invention relates to pyrimidines of formula (I)

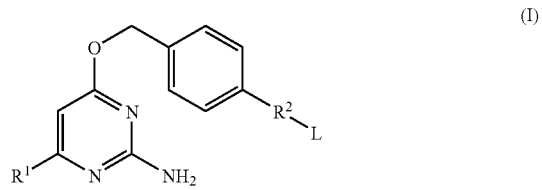

wherein $R^1$ is hydrogen, lower alkyl, halogen, cyano, trifluoromethyl or azido; $R^2$ is a linker; and L is a label or a plurality of same or different labels.

These compounds of formula (I) are suitable as substrates for $O^6$-alkylguanine-DNA alkyltransferases (AGT). The invention further relates to methods of transferring a label from pyrimidines of formula (I) to $O^6$-alkylguanine-DNA alkyltransferases (AGT) and AGT fusion proteins.

DETAILED DESCRIPTION OF THE INVENTION

Figure 1:
FIG. 1: CHO-SNAP26-NLS3 cells labeled with BG-TMR and compounds 17 and 18, see Example 20, exposure time 3 sec, magnification 40×.
(A) $O^6$-[(5(6)-carboxytetramethylrhodamine)-amidomethyl]-benzylguanine, BG-TMR
(B) N-[4-(2-Amino-4-chloropyrimidin-6-yloxymethyl)-benzyl]-tetramethylrhodamine-6-carboxamide 17
(C) N-[4-(2-Amino-4-chloropyrimidine-5-yloxymethyl)-benzyl]-tetramethylrhodamine-6-carboxamide 18.
Figure 1:
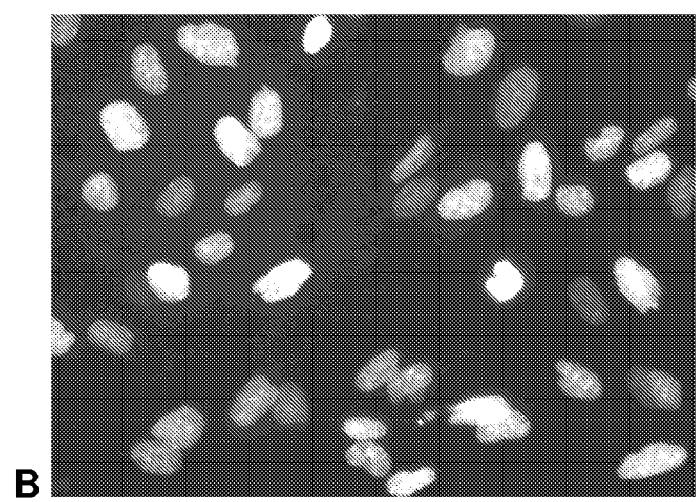
Figure 1:
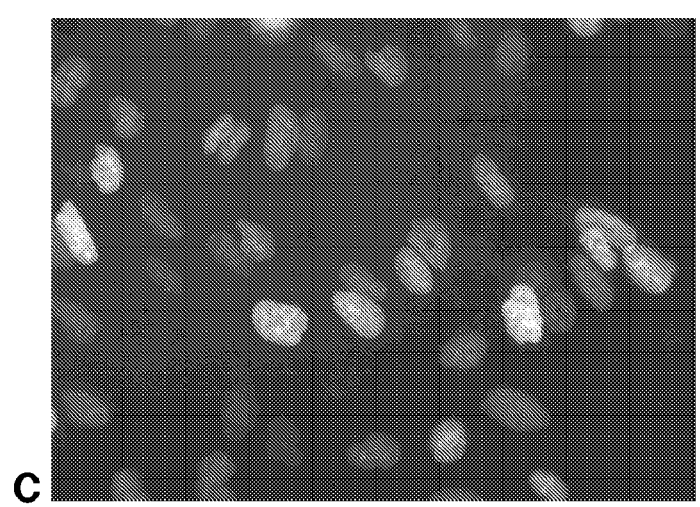
Figure 2:
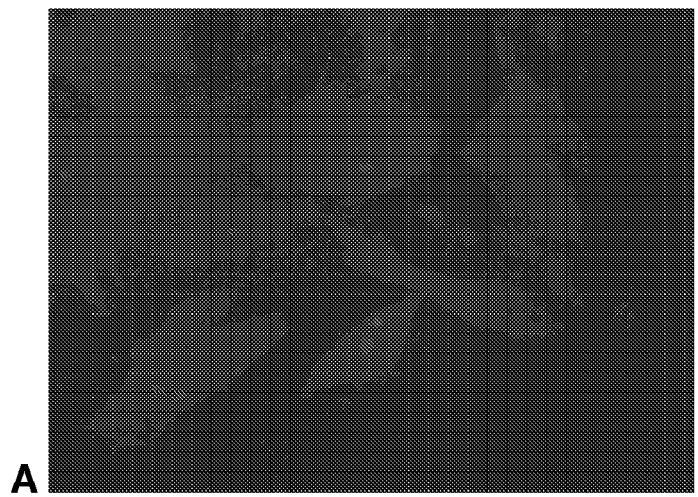
FIG. 2: CHO-SNAP26-F cells labeled with BG-TMR and compounds 17 and 18, see Example 20, exposure time 3 sec, magnification 40×.
(A) BG-TMR; (B) 17; (C) 18.
Figure 2:
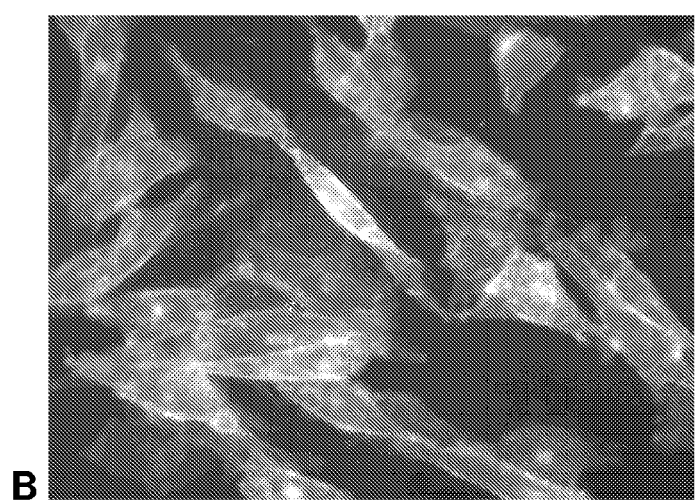
Figure 2:
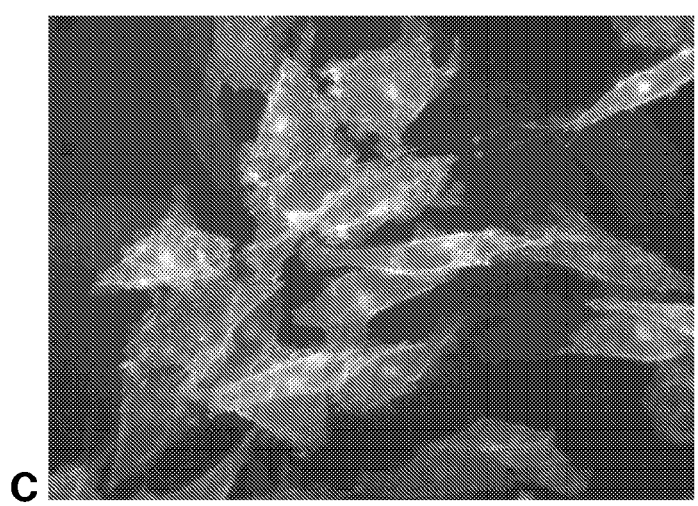
Figure 3:
FIG. 3: CHO-SNAP26-NLS3 cells labeled with BG-TMR and compounds 7 and 8, see Example 20, exposure time 3 sec, magnification 40×.
(A) BG-TMR
(B) N-[4-(2-Aminopyrimidin-4-yloxymethyl)-benzyl]-tetramethylrhodamine-6-carboxamide 7
(C) N-[4-(2-Aminopyrimidin-4-yloxymethyl)-benzyl]-tetramethylrhodamine-5-carboxamide 8.
Figure 3:
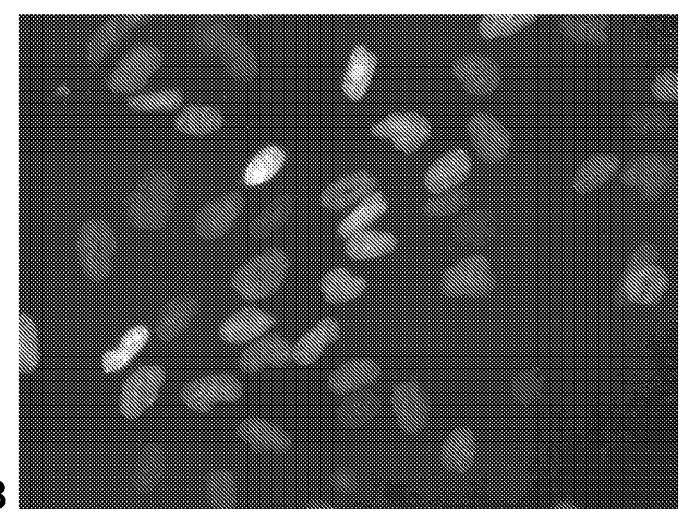
Figure 3:
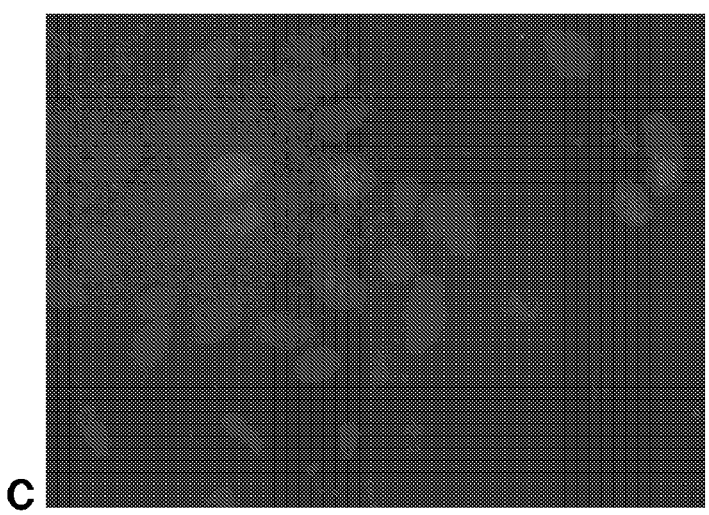
Figure 4:
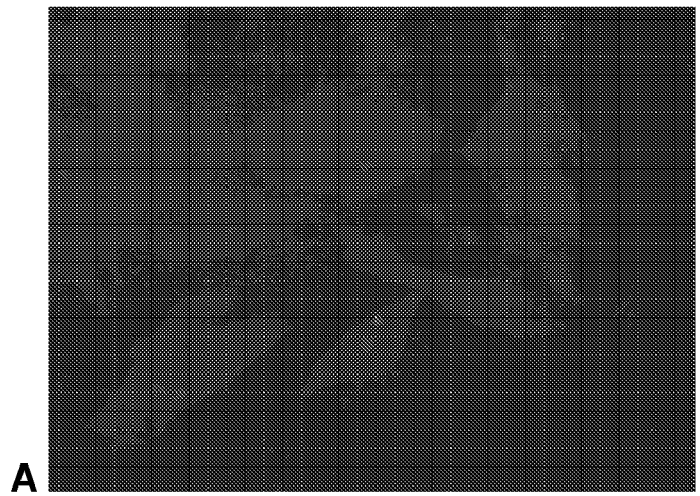
FIG. 4: CHO-SNAP26-F cells labeled with BG-TMR and compounds 17 and 18, see Example 20, exposure time 3 sec, magnification 40×.
(A) BG-TMR; (B) 7; (C) 8.
Figure 4:
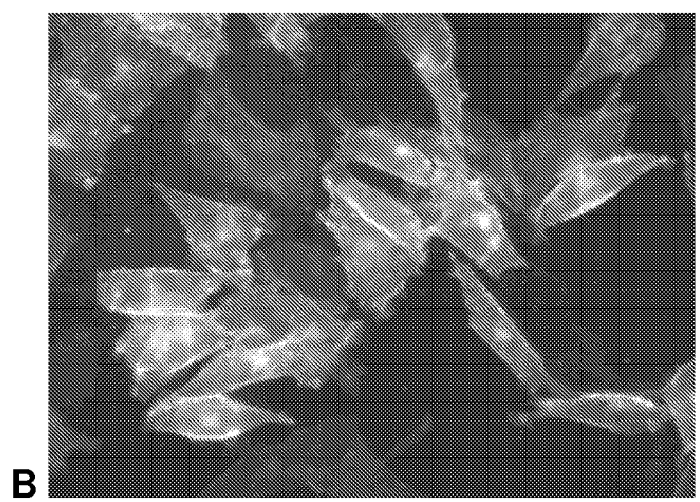
Figure 4:
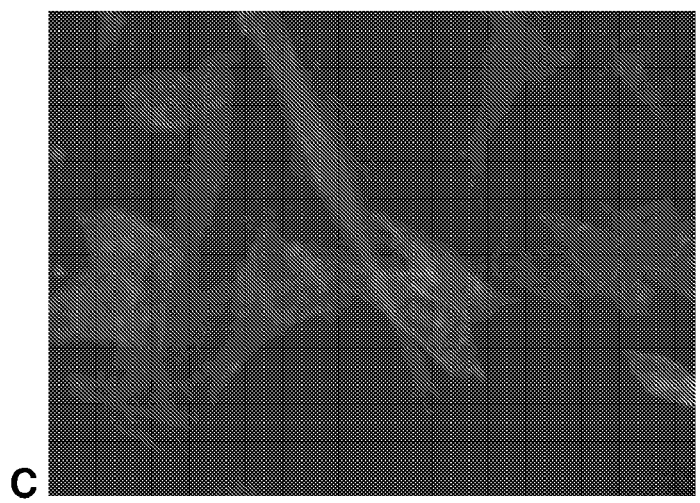
Figure 5:
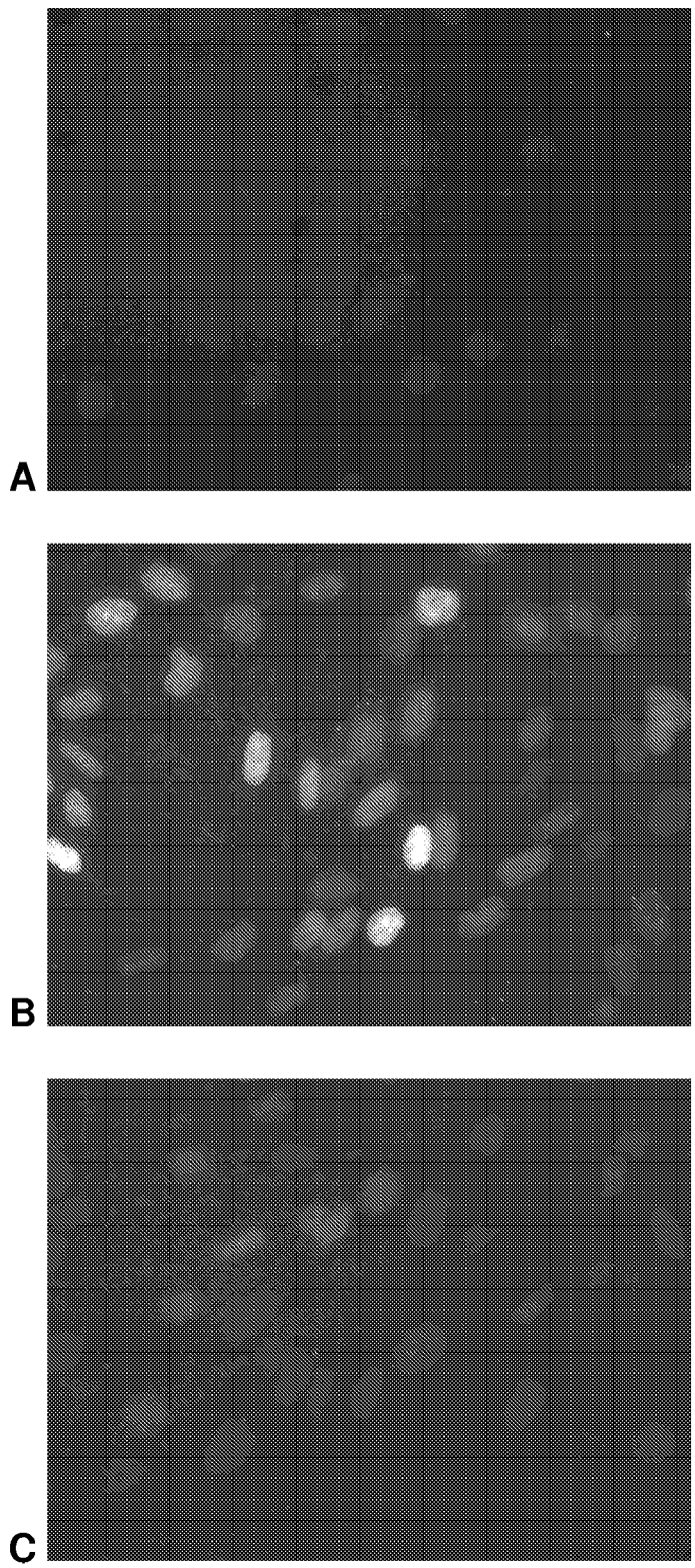
FIG. 5: CHO-SNAP26-NLS3 cells labeled with BG-TMR and compounds 12 and 13, see Example 20, exposure time 3 sec, magnification 40×.
(A) BG-TMR
(B) N-[4-(2-Amino-4-methyl-pyrimidin-6-yloxymethyl)-benzyl]-tetramethylrhodamine-6-carboxamide 12
(C) N-[4-(2-Amino-4-methyl-pyrimidin-6-yloxymethyl)-benzyl]-tetramethylrhodamine-5-carboxamide 13.
Figure 6:
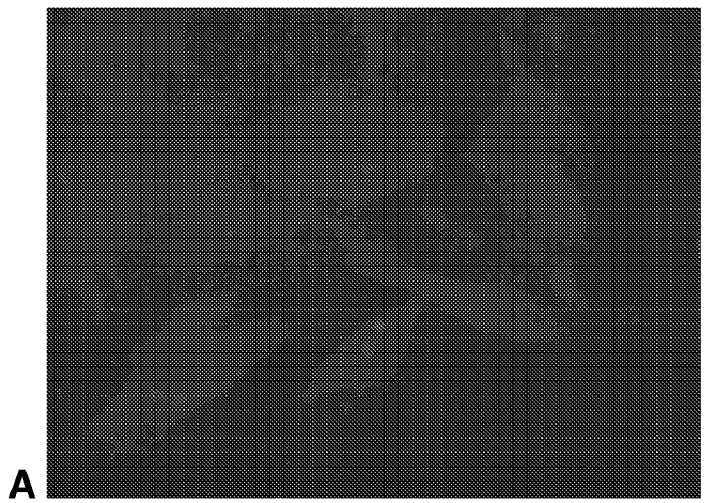
FIG. 6: CHO-SNAP26-F cells labeled with BG-TMR and compounds 12 and 13, see Example 20, exposure time 3 sec, magnification 40×.
(A) BG-TMR; (B) 12; (C) 13.
Figure 6:
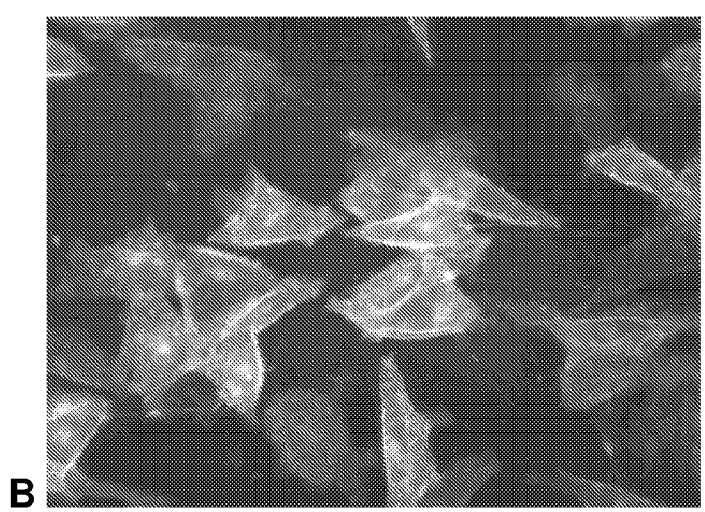
Figure 6:
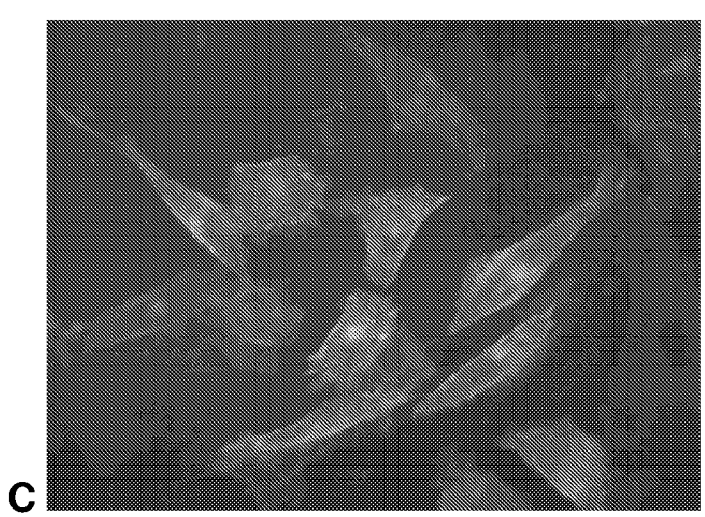

The particular pyrimidines suitable as AGT substrates are compounds of formula (I)

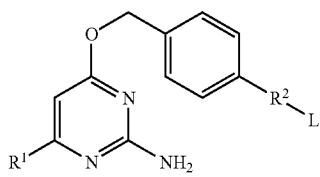

(I)

wherein R¹ is hydrogen, lower alkyl, halogen, cyano, trifluoromethyl or azido; R² is a linker; and L is a label or a plurality of same or different labels.

Lower alkyl is preferably alkyl with 1 to 7, preferably from 1 to 4 C atoms, and is linear or branched; preferably, lower alkyl is butyl, such as n-butyl, sec-butyl, isobutyl, tert-butyl, propyl, such as n-propyl or isopropyl, ethyl or methyl. Most preferably, lower alkyl is methyl.

Halogen is fluoro, chloro, bromo or iodo, in particular chloro or bromo, preferably chloro.

Preferred are compounds wherein R¹ is hydrogen, methyl or chloro, in particular methyl. Likewise preferred are compounds wherein R¹ is trifluoromethyl.

A linker group R² is preferably a flexible linker connecting a label L or a plurality of same or different labels to the benzyl group of the pyrimidines of the invention. Linker units are chosen in the context of the envisioned application, i.e. in the transfer of the substrate to a fusion protein comprising AGT. They also increase the solubility of the substrate in the appropriate solvent. The linkers used are chemically stable under the conditions of the actual application. The linker does not interfere with the reaction with AGT nor with the detection of the label L, but may be constructed such as to be cleaved at some point in time after the reaction of the compound of formula (I) with the fusion protein comprising AGT.

A linker R² is a straight or branched chain alkylene group with 1 to 300 carbon atoms, wherein optionally
(a) one or more carbon atoms are replaced by oxygen, in particular wherein every third carbon atom is replaced by oxygen, e.g. a polyethyleneoxy group with 1 to 100 ethyleneoxy units;
(b) one or more carbon atoms are replaced by nitrogen carrying a hydrogen atom, and the adjacent carbon atoms are substituted by oxo, representing an amide function —NH—CO—;
(c) one or more carbon atoms are replaced by oxygen, and the adjacent carbon atoms are substituted by oxo, representing an ester function —O—CO—;
(d) the bond between two adjacent carbon atoms is a double or a triple bond, representing a function —CH=CH— or —C≡C—;
(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;
(f) two adjacent carbon atoms are replaced by a disulfide linkage —S—S—; or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

Further substituents considered are e.g. those obtained when an α-amino acid, in particular a naturally occurring α-amino acid, is incorporated in the linker R² wherein carbon atoms are replaced by amide functions —NH—CO— as defined under (b). In such a linker, part of the carbon chain of the alkylene group R² is replaced by a group —(NH—CHR—CO)$_n$— wherein n is between 1 and 100 and R represents a varying residue of an α-amino acid.

A further substituent is one which leads to a photocleavable linker R², e.g. an o-nitrophenyl group. In particular this substituent o-nitrophenyl is located at a carbon atom adjacent to an amide bond, e.g. in a group —NH—CO—CH₂—CH(o-nitrophenyl)NH—CO—, or as a substituent in a polyethylene glycol chain, e.g. in a group —O—CH₂—CH(o-nitrophenyl)-O—. Other photocleavable linkers considered are e.g. phenacyl, alkoxybenzoin, benzylthioether and pivaloyl glycol derivatives.

A phenylene group replacing carbon atoms as defined under (e) hereinbefore is e.g. 1,2-, 1,3-, or preferably 1,4-phenylene. In a particular embodiment, the phenylene group is further substituted by a nitro group, and, combined with other replacements as mentioned above under (a), (b), (c), (d), and (f), represents a photocleavable group, and is e.g. 4-nitro-1,3-phenylene, such as in —CO—NH—CH₂-(4-nitro-)1,3-phenylene-CH(CH₃)—O—CO—, or 2-methoxy-5-nitro-1,4-phenylene, such as in —CH₂—O-(2-methoxy-5-nitro-)1,4-phenylene-CH(CH₃)—O—, or 2-nitro-1,4-phenylene, such as in —CO—O—CH₂-nitro-)1,4-phenylene-CO—NH—. Other particular embodiments representing photocleavable linkers are e.g. -1,4-phenylene-CO—CH₂—O—CO—CH₂— (a phenacyl group), -1,4-phenylene-CH(OR)CO-1,4-phenylene-(an alkoxybenzoin), or -3,5-dimethoxy-1,4-phenylene-CH₂—O— (a dimethoxy-benzyl moiety). A saturated or unsaturated cycloalkylene group replacing carbon atoms as defined under (e) hereinbefore is derived from cycloalkyl with 3 to 7 carbon atoms, preferably from cyclopentyl or cyclohexyl, and is e.g. 1,2- or 1,3-cyclopentylene, 1,2-, 1,3-, or preferably 1,4-cyclohexylene, or also 1,4-cyclohexylene being unsaturated e.g. in 1- or in 2-position. A saturated or unsaturated bicycloalkylene group replacing carbon atoms as defined under (e) hereinbefore is derived from bicycloalkyl with 7 or 8 carbon atoms, and is e.g. bicyclo[2.2.1]heptylene or bicyclo[2.2.2]octylene, preferably 1,4-bicyclo[2.2.1]heptylene optionally unsaturated in 2-position or doubly unsaturated in 2- and 5-position, and 1,4-bicyclo[2.2.2]-octylene optionally unsaturated in 2-position or doubly unsaturated in 2- and 5-position. A bridging heteroaromatic group replacing carbon atoms as defined under (e) hereinbefore is e.g. triazolidene, preferably 1,4-triazolidene, or isoxazolidene, preferably 3,5-isoxazolidene. A bridging saturated or unsaturated heterocyclyl group replacing carbon atoms as defined under (e) hereinbefore is e.g. derived from an unsaturated heterocyclyl group as defined under R₃ above, e.g. isoxazolidinene, preferably 3,5-isoxazolidinene, or a fully saturated heterocyclyl group with 3 to 12 atoms, 1 to 3 of which are heteroatoms selected from nitrogen, oxygen and sulfur, e.g. pyrrolidinediyl, piperidinediyl, tetrahydrofuranediyl, dioxane-diyl, morpholinediyl or tetrahydrothiophenediyl, preferably 2,5-tetrahydrofuranediyl or 2,5-dioxanediyl. A particular heterocyclyl group considered is a saccharide moiety, e.g. an α- or β-furanosyl or α- or β-pyranosyl moiety.

Cyclic substructures in a linker R² reduce the molecular flexibility as measured by the number of rotatable bonds within R², which leads to a better membrane permeation rate, important for all in vivo cell culture labeling applications.

A linker R² is preferably a straight chain alkylene group with 1 to 25 carbon atoms or a straight chain polyethylene glycol group with 4 to 100 ethyleneoxy units, optionally attached to the group A or R₃, respectively, by a —CH=CH— or —C≡C— group. Further preferred is a straight chain alkylene group with 1 to 25 carbon atoms wherein carbon atoms are optionally replaced by an amide function —NH—CO—, and optionally carrying a photocleavable subunit, e.g. o-nitrophenyl. Further preferred are branched linkers comprising a polyethylene glycol group of 3 to 6 ethylene glycol units and alkylene groups wherein carbon atoms are replaced by amide bonds, and further carrying substituted amino and hydroxy functions. Other preferred branched linkers have dendritic (tree-like) structures wherein amine, carboxamide and/or ether functions replace carbon atoms of an alkylene group.

A particularly preferred linker $R^2$ is a straight chain alkylene group of 2 to 40 carbon atoms optionally substituted by oxo wherein one or two carbon atoms are replaced by nitrogen and 0 to 12 carbon atoms are replaced by oxygen.

A most preferred linker $R^2$ is a straight chain alkylene group of 2 to 10 carbon atoms wherein one or two carbon atoms are replaced by nitrogen and one or two adjacent carbon atom are substituted by oxo, for example a linker —CH$_2$—NH(C=O) or —CH$_2$—NH(C=O)—(CH$_2$)$_5$—NH—.

A linker $R^2$ may carry one or more same or different labels, e.g. 1 to 100 same or different labels, in particular 1 to 5, preferably one, two or three, in particular one or two same or different labels.

The label L can be chosen by those skilled in the art dependent on the application for which the fusion protein is intended. Labels may be e.g. such that the labelled fusion protein carrying label L is easily detected or separated from its environment. Other labels considered are those which are capable of sensing and inducing changes in the environment of the labelled fusion protein and/or the substrate, or labels which aid in manipulating the fusion protein by the physical and/or chemical properties of the substrate and specifically introduced into the fusion protein.

Examples of a label L include a spectroscopic probe such as a fluorophore or a chromophore, a magnetic probe or a contrast reagent; a radioactively labelled molecule; a molecule which is one part of a specific binding pair which is capable of specifically binding to a partner; a molecule that is suspected to interact with other biomolecules; a library of molecules that are suspected to interact with other biomolecules; a molecule which is capable of crosslinking to other molecules; a molecule which is capable of generating hydroxyl radicals upon exposure to H$_2$O$_2$ and ascorbate, such as a tethered metal-chelate; a molecule which is capable of generating reactive radicals upon irradiation with light, such as malachite green; a molecule covalently attached to a solid support, where the support may be a glass slide, a microtiter plate or any polymer known to those proficient in the art; a nucleic acid or a derivative thereof capable of undergoing base-pairing with its complementary strand; a lipid or other hydrophobic molecule with membrane-inserting properties; a biomolecule with desirable enzymatic, chemical or physical properties; or a molecule possessing a combination of any of the properties listed above.

Further labels L are positively charged linear or branched polymers which are known to facilitate the transfer of attached molecules over the plasma membrane of living cells. This is of particular importance for substances which otherwise have a low cell membrane permeability or are in effect impermeable for the cell membrane of living cells. A non cell permeable AGT substrate will become cell membrane permeable upon conjugation to such a group L. Such cell membrane transport enhancer groups L comprise, for example, a linear poly(arginine) of D- and/or L-arginine with 6-15 arginine residues, linear polymers of 6-15 subunits which each carry a guanidinium group, oligomers or short-length polymers of from 6 to up to 50 subunits, a portion of which have attached guanidinium groups, and/or parts of the sequence of the HIV-tat protein, in particular the subunit Tat49-Tat57 (RKKRRQRRR in the one letter amino acid code). The pyrimidine of formula (I) is covalently linked to this group L through a linker $R^2$ as defined hereinbefore, which is preferably labile inside a living cell and may be degraded, e.g. by cleavage of an ester group $R^2$ by intracellular esterases, leading directly or in a further reaction provoked by the cleavage of the ester function to a separation of the AGT substrate and the unit L enhancing cell membrane permeability.

Most preferred as labels L are spectroscopic probes, and molecules which are one part of a specific binding pair which is capable of specifically binding to a partner, so-called affinity labels.

When the label L is a fluorophore, a chromophore, a magnetic label, a radioactive label or the like, detection is by standard means adapted to the label and whether the method is used in vitro or in vivo in cell culture and in tissue samples. If L is a fluorophore the method can be compared to the applications of the green fluorescent protein (GFP) which is genetically fused to a protein of interest and allows protein investigation in the living cell. Particular examples of labels L are also boron compounds displaying non-linear optical properties.

Depending on the properties of the label L, the fusion protein comprising protein of interest and AGT may be bound to a solid support on reaction with the substrate. The label L of the substrate reacting with the fusion protein comprising AGT may already be attached to a solid support when entering into reaction with AGT, or may subsequently, i.e. after transfer to AGT, be used to attach the labelled AGT fusion protein to a solid support. The label may be one member of a specific binding pair, the other member of which is attached or attachable to the solid support, either covalently or by any other means. A specific binding pair considered is e.g. biotin and avidin or streptavidin. Either member of the binding pair may be the label L of the substrate, the other being attached to the solid support. Further examples of labels allowing convenient binding to a solid support are e.g. maltose binding protein, glycoproteins, FLAG tags, or reactive substituents allowing chemoselective reaction between such substituent with a complementary functional group on the surface of the solid support. Examples of such pairs of reactive substituents and complementary functional group are e.g. amine and activated carboxy group forming an amide, azide and a propiolic acid derivative undergoing a 1,3-dipolar cycloaddition reaction, amine and another amine functional group reacting with an added bifunctional linker reagent of the type of activated bis-dicarboxylic acid derivative giving rise to two amide bonds, or other combinations known in the art.

Examples of a convenient solid support are e.g. glass surfaces such as glass slides, microtiter plates, and suitable sensor elements, in particular functionalized polymers (e.g. in the form of beads), chemically modified oxidic surfaces, e.g. silicon dioxide, tantalum pentoxide or titanium dioxide, or also chemically modified metal surfaces, e.g. noble metal surfaces such as gold or silver surfaces. Irreversibly attaching and/or spotting AGT substrates may then be used to attach AGT fusion proteins in a spatially resolved manner, particularly through spotting, on the solid support representing protein microarrays, DNA microarrays or arrays of small molecules.

When the label L is capable of generating reactive radicals, such as hydroxyl radicals, upon exposure to an external stimulus, the generated radicals can then inactivate the AGT fusion proteins as well as those proteins that are in close proximity of the AGT fusion protein, allowing to study the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI). In the present invention, labeling AGT fusion proteins with substrates carrying chromophores as label $L_1$, such as malachite green, and subsequent laser irradiation inactivates the labelled AGT fusion protein as well as those proteins that interact with the AGT fusion protein in a time-controlled and spatially-resolved manner. This method can be applied both in vivo in cell culture or in vitro. Furthermore, proteins which are in close proximity of the AGT fusion protein can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

When the label L is a molecule that can cross-link to other proteins, e.g. a molecule containing functional groups such as maleimides, active esters or azides and others known to those proficient in the art, contacting such labelled AGT substrates with AGT fusion proteins that interact with other proteins (in vivo or in vitro) leads to the covalent cross-linking of the AGT fusion protein with its interacting protein via the label. This allows the identification of the protein interacting with the AGT fusion protein. Labels L for photo cross-linking are e.g. benzophenones. In a special aspect of cross-linking the label L is a molecule which is itself an AGT substrate leading to dimerization of the AGT fusion protein. The chemical structure of such dimers may be either symmetrical (homodimers) or unsymmetrical (heterodimers). Other labels L considered are for example fullerenes, boranes for neutron capture treatment, nucleotides or oligonucleotides, e.g. for self-addressing chips, peptide nucleic acids, and metal chelates, e.g. platinum chelates that bind specifically to DNA.

A particular biomolecule with desirable enzymatic, chemical or physical properties is methotrexate. Methotrexate is a tight-binding inhibitor of the enzyme dihydrofolate reductase (DHFR). Compounds of formula (I) wherein L is methotrexate belong to the well known class of so-called "chemical inducers of dimerization" (CIDs). Using fusion proteins of hAGT with the DNA-binding domain LexA, and adding DHFR with the transcriptional activation domain B42 to the in vivo cell culture labeling of the hAGT fusion protein with a compound of formula (I) wherein L is methotrexate induces the coupling ("dimerization") of the hAGT-LexA fusion protein and DHFR-B42 fusion protein, leading to spatial proximity of LexA and B42 and subsequent stimulation of transcription.

If the substrate carries two or more labels, these labels may be identical or different. Particular preferred combinations are two different affinity labels, or one affinity label and one chromophore label, in particular one affinity label and one fluorophore label, or a pair of spectroscopic interacting labels $L^1/L^2$, e.g. a FRET pair.

Preferred are compounds wherein L is a spectroscopic probe, a molecule representing one part of a specific binding pair, a molecule covalently attached to a solid support, and compounds wherein L is a cell membrane transport enhancer group.

Particularly preferred are compounds wherein L is a fluorophore, for example fluorescein, tetramethylrhodamine or rhodamine-green. Likewise preferred are compounds wherein L is biotin.

Most preferred are the compounds of the Examples.

The invention further relates to a method for detecting and/or manipulating a protein of interest, wherein the protein of interest is incorporated into an AGT fusion protein, the AGT fusion protein is contacted with particular AGT substrates carrying a label described hereinbefore, and the AGT fusion protein is detected and optionally further manipulated using the label in a system designed for recognising and/or handling the label.

In the method of the present invention a protein or peptide of interest is fused to an $O^6$-alkylguanine-DNA alkyltransferase (AGT). The protein or peptide of interest may be of any length and both with and without secondary, tertiary or quaternary structure, and preferably consists of at least twelve amino acids and up to 2000 amino acids. Examples of such protein or peptide of interest are e.g. enzymes, DNA-binding proteins, transcription regulating proteins, membrane proteins, nuclear receptor proteins, nuclear localization signal proteins, protein cofactors, small monomeric GTPases, ATP-binding cassette proteins, intracellular structural proteins, proteins with sequences responsible for targeting proteins to particular cellular compartments, proteins generally used as labels or affinity tags, and domains or subdomains of the aforementioned proteins. The protein or peptide of interest is preferably fused to AGT by way of a linker which may be cleaved by an enzyme, e.g. at the DNA stage by suitable restriction enzymes and/or linkers cleavable by suitable enzymes at the protein stage.

The $O^6$-alkylguanine-DNA alkyltransferase (AGT) has the property of transferring a label present on a substrate to one of the cysteine residues of the AGT forming part of a fusion protein. In preferred embodiments, the AGT is wild type human $O^6$-alkylguanine-DNA alkyltransferase, hAGT, or a mutant thereof, e.g. a mutant as described in Juillerat et al., Chem Biol 10:313-317, 2003, or in PCT/EP2005/050899. A mutant AGT to be used in the invention may differ from wild type hAGT by virtue of one or more, e.g. up to ten, amino acid substitutions, deletions or additions, but still retains the property of transferring a label present on a substrate to the AGT part of the fusion protein. A mutant AGT may preferably be produced using protein engineering techniques known to the skilled person in the art, e.g. saturation mutagenesis, error prone PCR to introduce variations anywhere in the sequence, or DNA shuffling used after saturation mutagenesis and/or error prone PCR.

The fusion protein comprising protein of interest and an $O^6$-alkylguanine-DNA alkyl-transferase (AGT) is contacted with a particular substrate having a label. Conditions of reaction are selected such that the AGT reacts with the substrate and transfers the label of the substrate. Usual conditions are a buffer solution at around pH 7 at room temperature, e.g. around 25° C. However, it is understood that AGT reacts also under a variety of other conditions, and those conditions mentioned here are not limiting the scope of the invention.

AGT irreversibly transfers the alkyl group from its natural substrate, $O^6$-alkylguanine-DNA, to one of its cysteine residues. Likewise, AGT transfers the substituted benzyl group connected to $O^4$ (or $O^6$, respectively) of the pyrimidine nucleus of formula (I) to one of its cysteine residues. This property of AGT is used in the method of the invention to transfer the label L as the residue $-CH_2-C_6H_4-R^2-L$ of a compound of formula (I) to AGT.

This label L of the substrate can be chosen by those skilled in the art dependent on the application for which the fusion protein is intended. After contacting the fusion protein comprising AGT with the substrate, the label L is covalently bonded to the fusion protein. The labelled AGT fusion protein is then further manipulated and/or detected by virtue of the transferred label. The label L may consist of a plurality of same or different labels. If the substrate contains more than one label L, the corresponding labelled AGT fusion protein will also comprise more than one label which gives more options for further manipulating and/or detecting the labelled fusion protein.

In vitro, the reaction of the AGT fusion protein with the substrate of the invention can generally be either performed in cell extracts or with purified or enriched forms of the AGT fusion protein.

If experiments with the substrates of the present invention are done in vivo in cell culture or in cell extracts, the reaction of the endogenous AGT of the host is advantageously taken into account. If the endogenous AGT of the host does not accept pyrimidines of formula (I) as a substrate, the reaction of the (exogenous) AGT fusion protein is specific. In mammalian cells, e.g. in human, murine, or rat cells, unspecific reaction with endogenous AGT is possible. In those experiments where the simultaneous reaction of the endogenous AGT as well as of the (exogenous) AGT fusion protein poses a problem, known AGT-deficient cell lines can be used.

The experiments are preferably accomplished outside the human or animal body. In particular they are performed in vitro or in vivo in cell culture.

Method of Manufacture

Pyrimidines of the invention are generally prepared by standard methods known in the art. The present invention also relates to new methods as described hereinafter, and to novel intermediates used and obtained.

In particular, compounds of formula (I) are prepared by (A) reaction of a compound of formula (II)

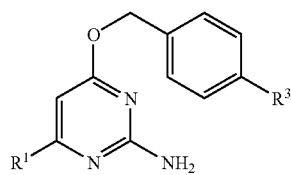

wherein $R^1$ has the meaning as defined under formula (I) and $R^3$ is a linker group as defined under formula (I) for $R^2$ further carrying a reactive functional group, with a label L as defined under formula (I) or a reactive derivative thereof, or (B) reaction of a compound of formula (III)

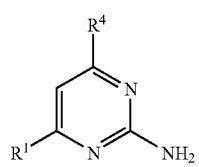

wherein $R^1$ has the meaning as defined under formula (I) and $R^4$ is a reactive functional group,
with an alcoholate of formula

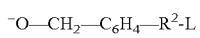

$^-O$—$CH_2$—$C_6H_4$—$R^2$-L  (IV)

and, if so desired, an obtainable compound of formula (I) is converted into another compound of formula (I), a free compound of formula (I) is converted into a salt, an obtainable salt of a compound of formula (I) is converted into the free compound or another salt, and/or a mixture of isomeric compounds of formula (I) is separated into the individual isomers.

In process (A), a further reactive functional group in substituent $R^3$ is, for example, an amino, hydroxy or thio group, which may react with a carboxy function in L, or a carboxy group, which may react with an amino, hydroxy or thio function in label L. Reaction conditions may be chosen in accordance with the corresponding reactive groups, and are, for example those known in protein chemistry to combine amino functions with (activated) carboxy groups. Activated carboxy groups are, for example, N-succinimidyl esters. The reaction is usually carried out in the presence of a suitable solvent, with cooling or heating, for example in a temperature range from approximately −30° C. to approximately +150° C., especially approximately around 0° C. to room temperature In process (B), the reactive group $R^4$ is a halogen, for example chloro or bromo, or an ammonium group, for example trimethylammonium or methylpyrrolidinium, easily substitutable in an $S_N2$-type reaction. Preferred as the reactive group is chloro. Reaction conditions may be chosen in accordance with the corresponding reactive groups, and are, for example, those known to be suitable in $S_N2$-type substitution reactions. The reaction can be carried out in a manner known per se, usually in the presence of a base, and usually in the presence of a suitable solvent, with cooling or heating, for example in a temperature range from approximately −30° C. to approximately +150° C., especially approximately around 0° C. to room temperature. The alcoholate of compound (IV) is preferably formed in situ from the corresponding benzylic alcohol by a suitable base, for example a trisubstituted amine such as triethyl amine, dimethylaniline, pyridine or diethylisopropylamine, or preferably by reaction with sodium hydride.

Suitable solvents are polar, inert solvents, e.g. an ether such as tetrahydrofuran, or a dipolar aprotic solvent such as dimethylformamide, dimethyl sulfoxide, or, preferably, dimethyl-acetamide.

If one or more other functional groups, for example carboxy, hydroxy or amino, are or need to be protected in a compound of formula (II), (III), (IV) or in a label L, because they should not take part in the reaction, these are such protecting groups as are usually applied in the synthesis of amides, in particular peptide compounds, cephalosporins, penicillins, nucleic acid derivatives and sugars. The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as T. W. Greene and P. G. M. Wuts, "Protective Groups in Organic Synthesis", Wiley, 3$^{rd}$ edition 1999.

Salts of a compound of formula (I) with a salt-forming group may be prepared in a manner known per se. Acid addition salts of compounds of formula (I) may thus be obtained by treatment with an acid or with a suitable anion exchange reagent.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to +60° C., at −20 to +40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers, regioisomers or enantiomers, or into any mixtures of isomers, e.g. racemates or diastereomeric mixtures.

In the preferred embodiment, a compound of formula (I) is prepared according to or in analogy to the processes and process steps defined in the Examples.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of formula (II) are known, commercially available, or can be synthesized in analogy to or according to methods that are known in the art, for example in analogy to process (B). Corresponding starting materials of formula (III) and (IV) are likewise known, commercially available, or can be synthesized in analogy to or according to methods that are known in the art.

EXAMPLES

Example 1

2-Amino-4-chloropyrimidine (2) and 4-amino-2-chloropyrimidine (3)

A suspension of 2,4-dichloropyrimidine (7.45 g, 50.0 mmol) in ammonium hydroxide (25%, 125 mL) is stirred at room temperature for 5 h. The appearance of the insoluble material changes from "salt-like" to "snow-like". The precipitate is collected by filtration and dried in vacuo. The crude material is redissolved in MeOH:CH$_2$Cl$_2$ (1:1), adsorbed on SiO$_2$ and purified by column chromatography (gradient cyclohexane:ethyl acetate from 5:1 to 1:1) to yield 1.48 g (23%) of 2 and 1.73 g (26%) of 3 (TLC cyclohexane:ethyl acetate 3:1, R$_f$ (2)=0.45, R$_f$ (3)=0.32). ESI-MS m/z 129.8 [M+H]$^+$.

Example 2

N-[4-(2-Amino-pyrimidin-4-yloxymethyl)-benzyl]-2,2,2-trifluoro-acetamide (5)

252 mg (1.15 mmol) 2,2,2-trifluoro-N-(4-hydroxymethyl-benzyl)-acetamide is dissolved in 2 mL dry dimethylacetamide under argon atmosphere, and 56 mg (2.31 mmol) NaH is added. 100 mg (0.77 mmol) 2-amino-4-chloro-pyrimidine (2) is added and the solution stirred at room temperature over night. 1 mL water is added carefully to quench all excess NaH and the mixture poured into 50 ml of 0.5 N HCl. The crude product is extracted with ethyl acetate, the combined organic phases washed with brine and dried over MgSO$_4$. After evaporation of the solvent, the product is purified by flash column chromatography (ethyl acetate:cyclohexane 1:1). Yield: 160 mg (63%). ESI-MS m/z 327.4 [M+H]$^+$.

Example 3

4-(4-Aminomethyl-benzyloxy)-2-amino-pyrimidine (6)

50 mg (1.53 mmol) N-[4-(2-Amino-pyrimidin-4-yloxymethyl)-benzyl]-2,2,2-trifluoro-acetamide (5) is dissolved in 1 mL methanol and treated with 2 mL methylamine (33% in ethanol). The reaction mixture is stirred at room temperature over night and all volatiles are removed in vacuo. The product is used without further purification in the next step. ESI-MS m/z 231.4 [M+H]$^+$.

Example 4

N-[4-(2-Aminopyrimidin-4-yloxymethyl)-benzyl]-tetramethylrhodamine-6-carboxamide (7) and N-[4-(2-Aminopyrimidin-4-yloxymethyl)-benzyl]-tetramethylrhodamine-5-carboxamide (8)

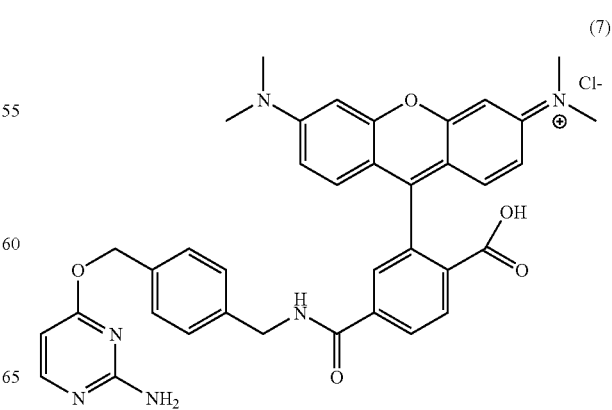

(7)

-continued

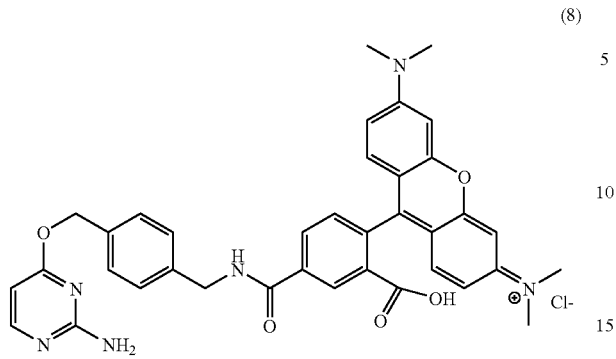

(8)

4-(4-Aminomethyl-benzyloxy)-2-aminopyrimidine (6, 8 mg, 0.03 mmol) and 5(6)-carboxytetramethylrhodamine succinimidyl ester (Molecular Probes, 7.47 mg, 0.014 mmol) are dissolved in 850 μL DMF with 20 μL TEA and left at room temperature for 24 h. The product is purified and the 5- and 6-isomers separated by reversed phase MPLC (medium pressure liquid chromatography) on a C18 column using a linear gradient of water:acetonitrile (from 95:5 to 20:80 in 20 min, 0.08% TFA). MS (ESI) m/z 658.8 [M−Cl]⁺.

Example 5

N-[4-(2-Amino-4-methylpyrimidin-6-yloxymethyl)-benzyl]-2,2,2-trifluoro-acetamide (10)

812 mg (3.48 mmol) 2,2,2-trifluoro-N-(4-hydroxymethyl-benzyl)-acetamide is dissolved in 3 mL dry dimethylacetamide under argon atmosphere, and 167 mg (6.96 mmol) NaH is added over 5 min. 500 mg (3.48 mmol) 2-amino-4-chloro-6-methylpyrimidine is then added and the solution stirred at 90° C.— over night. 1 mL water is added carefully to quench all excess NaH, and the mixture poured into 50 ml of 0.5 N HCl. The crude product is extracted with ethyl acetate, the combined organic phases washed with brine and dried over MgSO₄. After evaporation of the solvent, the product is purified by flash column chromatography (gradient ethyl acetate: cyclohexane from 1:1 to 3:1). Yield: 350 mg (29%). ESI-MS m/z 341.7 [M+H]⁺.

Example 6

6-(4-Aminomethyl-benzyloxy)-2-amino-4-methylpyrimidine (11)

15 mg (0.061 mmol) N-[4-(2-Amino-4-methylpyrimidin-6-yloxymethyl)-benzyl]-2,2,2-trifluoro-acetamide is dissolved in 1 mL methanol and treated with 2 mL methylamine (33% in ethanol). The reaction mixture is stirred at room temperature over night and all volatiles are removed in vacuo. The product is used without further purification in the next step. ESI-MS m/z 245.1 [M+H]⁺.

Example 7

N-[4-(2-Amino-4-methylpyrimidin-6-yloxymethyl)-benzyl]-tetramethylrhodamine-6-carboxamide (12) and N-[4-(2-Amino-4-methylpyrimidin-6-yloxymethyl)-benzyl]-tetramethylrhodamine-5-carboxamide (13)

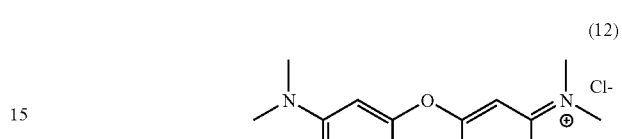

(12)

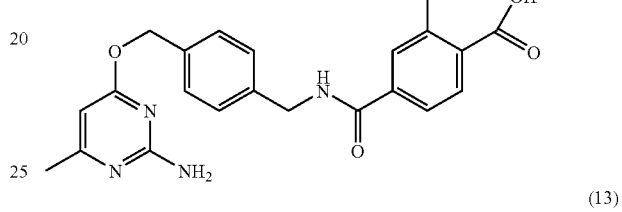

(13)

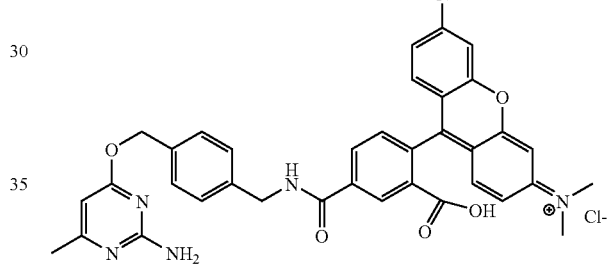

6-(4-Aminomethyl-benzyloxy)-2-amino-4-methylpyrimidine (11, 8 mg, 0.03 mmol) and 5(6)-carboxytetramethylrhodamine succinimidyl ester (Molecular Probes, 7.47 mg, 0.014 mmol) are dissolved in 850 μL DMF with 20 μL TEA and left at room temperature for 24 h. The product is purified and the 5 and 6 isomers separated by reversed phase MPLC on a C18 column using a linear gradient water:acetonitrile (from 95:5 to 20:80 in 20 min, 0.08% TFA). MS (ESI) m/z 658.8 [M−Cl]⁺.

Example 8

N-[4-(2-Amino-4-chloropyrimidin-6-yloxymethyl)-benzyl]-2,2,2-trifluoro-acetamide (15)

356 mg (1.52 mmol) 2,2,2-trifluoro-N-(4-hydroxymethyl-benzyl)-acetamide is dissolved in 3 mL dry dimethylacetamide under argon atmosphere, and 73.1 mg (3.1 mmol) NaH is added. 250 mg-(1.54 mmol) 2-amino-4,6-dichloropyrimidine is then added and the solution stirred at 90° C. over night. 1 mL water is added carefully to quench all excess NaH and the mixture poured into 50 mL 0.5 N HCl. The crude product is extracted with ethyl acetate, the combined organic phases washed with brine and dried over MgSO₄. After evaporation of the solvent, the product is purified by flash column chromatography (gradient ethyl acetate:cyclohexane from 1:1 to 3:1). Yield: 254 mg (46%). ESI-MS m/z 361.1 [M+H]⁺.

Example 9

6-(4-Aminomethyl-benzyloxy)-2-amino-4-chloropyrimidine (16)

65 mg (0.18 mmol) N-[4-(2-amino-4-chloropyrimidin-6-yloxymethyl)-benzyl]-2,2,2-trifluoro-acetamide (15) is dissolved in 1 mL methanol and treated with 2 mL methylamine (33% in ethanol). The reaction mixture is stirred at room temperature over night and all volatiles are removed in vacuo. The product is used without further purification in the next step. ESI-MS m/z 265.3 [M+H]⁺.

Example 10

N-[4-(2-Amino-4-chloropyrimidin-6-yloxymethyl)-benzyl]-tetramethylrhodamine-6-carboxamide (17) and N-[4-(2-amino-4-chloropyrimidin-6-yloxymethyl)-benzyl]-tetramethylrhodamine-5-carboxamide (18)

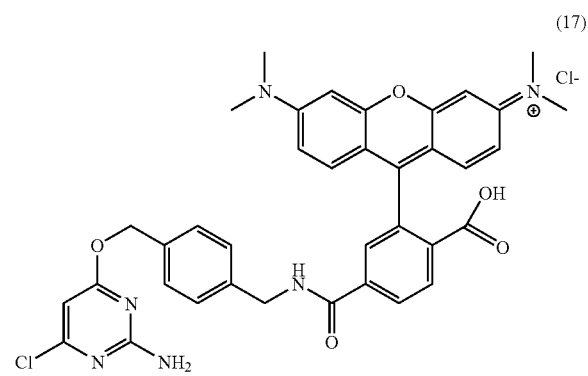

6-(4-Aminomethyl-benzyloxy)-2-amino-4-chloropyrimidine (16, 8 mg, 0.03 mmol) and 5(6)-carboxytetramethylrhodamine succinimidyl ester (7.47 mg, 0.014 mmol) are dissolved in 850 µL DMF with 20 µL TEA and left at room temperature for 24 h. The product is purified and the 5 and 6 isomers separated by reversed phase MPLC on a C18 column using a linear gradient water:acetonitrile (from 95:5 to 20:80 in 20 min, 0.08% TFA). MS (ESI) m/z 714.7 [M–Cl]⁺.

Example 11

N-[4-(2-Amino-4-methylpyrimidin-6-yloxymethyl)-benzyl]-rhodamine-green-6-carboxamide (19)

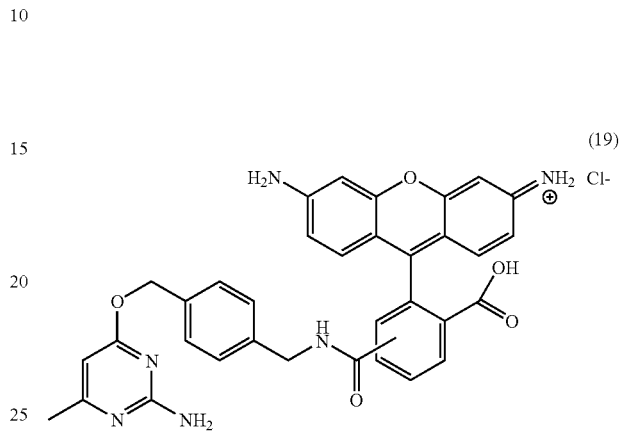

6-(4-Aminomethyl-benzyloxy)-2-amino-4-methylpyrimidine (11, 8 mg, 0.03 mmol) and 5(6)-carboxyrhodamine-green succinimidyl ester (Molecular Probes, 7.10 mg, 0.014 mmol) are dissolved in 850 µL DMF with 20 µL TEA and left at room temperature for 24 h. The product is purified by reversed phase MPLC on a C18 column using a linear gradient water:acetonitrile (from 95:5 to 20:80 in 20 min, 0.08% TFA). MS (ESI) m/z 602.5 [M–Cl]⁺.

Example 12

N-[4-(2-Amino-pyrimidin-4-yloxymethyl)-benzyl]-6-biotinylamino-hexanoylcarboxamide (21)

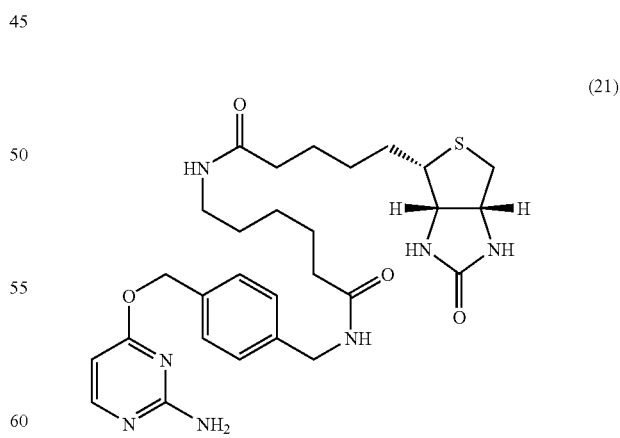

4-(4-Aminomethyl-benzyl)-2-aminopyrimidine (6, 3.5 mg, 0.015 mmol) and N-(+)-biotinyl-aminocaproic acid succinimidyl ester (3.5 mg, 0.007 mmol) are dissolved in 300 µL DMF with 4 µL TEA and left at room temperature for 24 h. The product is purified by reversed phase MPLC on a C18 column using a linear gradient water:acetonitrile (from 95:5 to 20:80 in 20 min, 0.08% TFA). MS (ESI) m/z 570.8 [M+H]$^+$.

Example 13

N-[4-(2-Amino-4-methylpyrimidin-6-yloxymethyl)-benzyl]-6-biotinylamino-hexanoylcarboxamide (22)

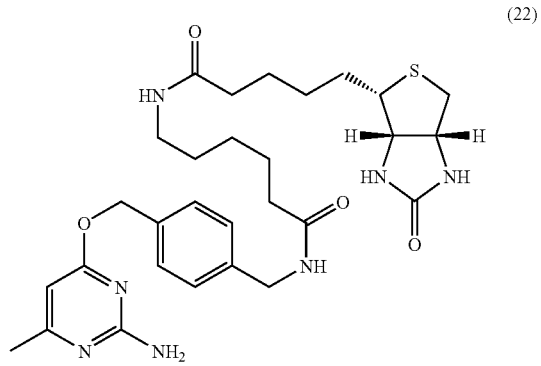

(22)

6-(4-Aminomethyl-benzyloxy)-2-amino-4-methylpyrimidine (11, 3.5 mg, 0.015 mmol) and N-(+)-biotinyl-aminocaproic acid succinimidyl ester (3.5 mg, 0.007 mmol) are dissolved in 300 μL DMF with 4 μL TEA and left at room temperature for 24 h. The product is purified by reversed phase MPLC on a C18 column using a linear gradient water:acetonitrile (from 95:5 to 20:80 in 20 min, 0.08% TFA). MS (ESI) m/z 584.8 [M+H]$^+$.

Example 14

N-[4-(2-Amino-4-chloropyrimidin-6-yloxymethyl)-benzyl]-6-biotinylamino-hexanoylcarboxamide (23)

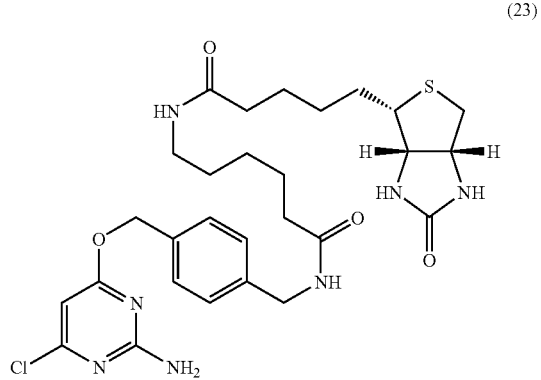

(23)

6-(4-Aminomethyl-benzyloxy)-2-amino-4-chloropyrimidine (16, 3.5 mg, 0.015 mmol) and N-(+)-biotinyl-aminocaproic acid succinimidyl ester (3.5 mg, 0.007 mmol) are dissolved in 300 μL DMF with 4 μL TEA and left at room temperature for 24 h. The product is purified by reversed phase MPLC on a C18 column using a linear gradient water:acetonitrile (from 95:5 to 20:80 in 20 min, 0.08% TFA). MS (ESI) m/z 604.2 [M+H]$^+$.

Example 15

4-chloro-6-(trifluoromethyl)pyrimidin-2-amine (24)

2-Amino-6-(trifluoromethyl)pyrimidin-4-ol (200 mg, 1.1 mmol) is dissolved in POCl$_3$ (3 eq., 0.3 mL, 3.3 mmol) and dimethylaniline (0.28 mL, 2 eq.) is added. The reaction mixture is heated at 70° C. for 4 h. The resulting mixture is poured into a mixture of ice-water, and the resulting precipitate is collected to yield the desired compound 24 in 59%. ESI-MS m/z 198 [M+H]$^+$.

Example 16

N-[4-(2-Amino-4-trifluoromethylpyrimidin-6-yloxymethyl)-benzyl]-2,2,2-trifluoro-acetamide (25)

322 mg (1.38 mmol) 2,2,2-trifluoro-N-(4-hydroxymethyl-benzyl)-acetamide is dissolved in 2 mL dry dimethylacetamide under argon atmosphere, and 50 mg (2.1 mmol) NaH is added. 136 mg (0.69 mmol) 4-chloro-6-(trifluoromethyl)pyrimidin-2-amine 24 is then added and the solution stirred at 90° C. over night. 1 mL water is added carefully to quench all excess NaH and the mixture poured into 50 mL 0.5 N HCl. The crude product is extracted with ethyl acetate, the combined organic phases washed with brine and dried over MgSO$_4$. After evaporation of the solvent, the product is purified by flash column chromatography (gradient ethyl acetate:cyclohexane from 1:1 to 3:1).

Example 17

6-(4-Aminomethyl-benzyloxy)-2-amino-4-trifluoropyrimidine (26)

50 mg (0.15 mmol) N-[4-(2-amino-4-trifluoropyrimidin-6-yloxymethyl)-benzyl]-2,2,2-trifluoro-acetamide (25) is dissolved in 1 mL methanol and treated with 2 mL methylamine (33% in ethanol). The reaction mixture is stirred at room temperature over night and all volatiles are removed in vacuo. The product is used without further purification in the next step.

Example 18

N-[4-(2-Amino-4-trifluoropyrimidin-6-yloxymethyl)-benzyl]-tetramethyl-rhodamine-6-carboxamide (27) and N-[4-(2-amino-4-trifluoropyrimidin-6-yloxymethyl)-benzyl]-tetramethylrhodamine-5-carboxamide (28)

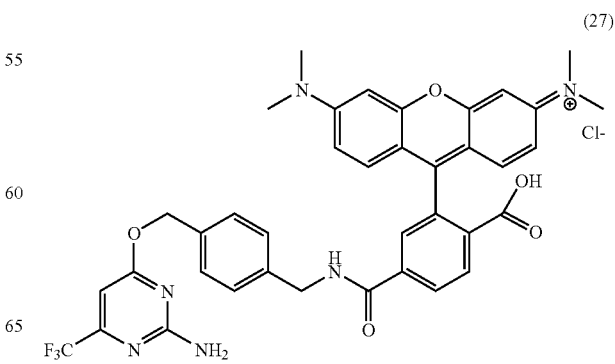

(27)

19

-continued (28)

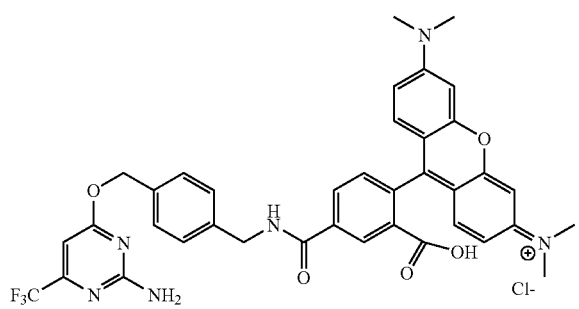

6-(4-Aminomethyl-benzyloxy)-2-amino-4-trifluoropyrimidine (26, 4.5 mg, 0.015 mmol) and 5(6)-carboxytetramethylrhodamine succinimidyl ester (2 mg, 0.0038 mmol) are dissolved in 420 μL DMF with 1 μL TEA and left at room temperature for 24 h. The product is purified and the 5 and 6 isomers separated by reversed phase MPLC on a C18 column using a linear gradient water:acetonitrile (from 95:5 to 20:80 in 20 min, 0.08% TFA). MS (ESI) m/z 711.1 [M−Cl]⁺.

Example 19

N-[4-(2-Amino-4-trifluoromethylpyrimidin-6-yloxymethyl)-benzyl]-rhodamine-green-6-carboxamide (29)

(29)

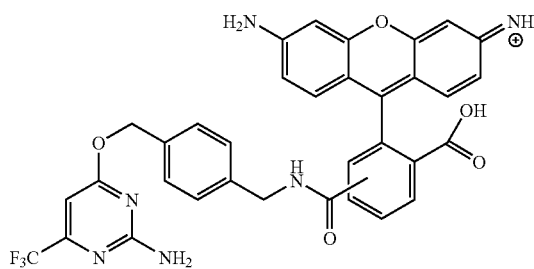

6-(4-Aminomethyl-benzyloxy)-2-amino-4-methylpyrimidine (26, 5.4 mg, 0.018 mmol) and 5(6)-carboxyrhodamine-green succinimidyl ester (Molecular Probes, 2.2 mg, 0.00433 mmol) are dissolved in 500 μL DMF with 1 μL TEA and left at room temperature for 24 h. The product is purified by reversed phase MPLC on a C18 column using a linear gradient water:acetonitrile (from 95:5 to 20:80 in 20 min, 0.08% TFA). MS (ESI) m/z 655.6 [M−Cl]⁺.

Example 20

Labeling Protocol for AGT Fusion Proteins

Fusions of the following modification of hAGT are used for generating stable transfections in CHO-cells deficient in hAGT: Cys62Ala, Lys125Ala, Ala127 Thr, Arg128Ala, Gly131 Lys, Gly132 Thr, Met134Leu, Arg135Ser, Cys150Ser, Asn157Gly, Ser159Glu, Truncation at 182 (SNAP26, see PCT/EP2005/050900 where this mutant hAGT is named AGT26).

SNAP26 is fused to 3 repeats of the SV40 virus nuclear localization sequence, resulting in SNAP26-NLS3, or else SNAP26 is fused to a farnesylation sequence resulting in SNAP26-F. In living cells SNAP26-F will be farnesylated and recruited thereafter to the cell membrane. Stable transfections of both genes are used to test the labeling performance of the pyrimidine compounds of formula (I) wherein L is a fluorophore. The cells are seeded in 24 well tissue culture plates and left over night to reattach. The tissue culture medium is replaced with labeling solution containing 5 μM of a compound of formula (I) in F12 Medium supplemented with 10% fetal calf serum. The cells are incubated at 37° C. in a $CO_2$ incubator for 30 min. After two washing steps with 500 μl F12 medium with 10% fetal calf serum, the cells are incubated for 30 min to allow unbound compounds of formula (I) to leak out of the cells. Cells are washed one more time before imaging under a Zeiss Axiovert 40 CFL epifluorescence microscope using a standard rhodamine-filter set for compounds of formula (I) wherein L is tetramethylrhodamine or a standard fluoresceine filter set wherein L is rhodamine green.

The invention claimed is:
1. A compound of formula (I)

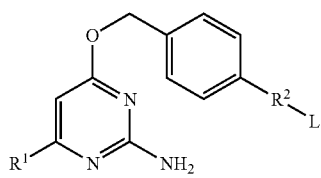

(I)

wherein $R^1$ is lower alkyl, halogen, cyano, trifluoromethyl or azido; $R^2$ is a linker; and L is a label or a plurality of same or different labels.

2. The compound according to claim 1 wherein $R^2$ is a straight or branched chain modified alkylene group with 1-300 carbon atoms, the alkylene group containing one or more modifications selected from the group consisting of:
    (a) replacement of one or more carbon atoms by oxygen or a polyethyleneoxy group;
    (b) replacement of one or more carbon atoms by an amide group;
    (c) replacement of one or two carbon atoms by nitrogen and 0-12 carbon atoms are replaced by oxygen;
    (d) replacement of one or more carbon atoms by an ester group;
    (e) a double or a triple bond between two adjacent carbons;
    (e) replacement of one or more carbon atoms by a phenylene, a saturated or unsaturated cycloalkylene, a saturated or unsaturated bicycloalkylene, a bridging heteroaromatic or a bridging saturated or an unsaturated heterocyclyl group; and
    (f) replacement of two adjacent carbon atoms by a disulfide linkage —S—S.

3. The compound according to claim 1 of formula (I) wherein L is one or a plurality of same or different labels selected from a spectroscopic probe, a magnetic probe, a contrast reagent, a molecule which is one part of a specific binding pair which is capable of specifically binding to a partner, a molecule that is capable of interacting with other biomolecules, a molecule which is capable of crosslinking to other molecules, a molecule which is capable of generating hydroxyl radicals upon exposure to $H_2O_2$ and ascorbate, a molecule which is capable of generating reactive radicals upon irradiation with light, a molecule covalently attached to a solid support, a lipid, or a cell membrane transport enhancer group.

4. The compound according to claim 1 of formula (I) wherein L is a spectroscopic probe.

5. The compound according to claim 4 wherein the spectroscopic probe is a fluorophore.

6. The compound according to claim 1 of formula (I) wherein $R^1$ is a lower alkyl group and the lower alkyl group is methyl or $R^1$ is a halogen and the halogen is a chloro.

7. The compound according to claim 1 of formula (I) wherein $R^1$ is a trifluoromethyl.

8. The compound according to claim 1 of formula (I) wherein $R^2$ is a linker —$CH_2$—NH(C═O)— or —$CH_2$—NH(C═O)—$(CH_2)_5$—NH—, and L is a fluorophore or biotin.

9. The compound according to claim 1 wherein $R^2$ is a linker —CH2-NH(C═O) and L is a fluorophore, wherein the fluorophore is tetramethylrhodamine or rhodamine green.

10. The compound according to claim 1 wherein $R^2$ is a linker —$CH_2$—NH(C═O)—$(CH_2)_5$—NH— and L is biotin.

11. A method for detecting a protein; comprising:
(a) incorporating a protein into an AGT fusion protein;
(b) contacting the AGT fusion protein with a compound of formula (I) according to claim 1; and
(c) detecting the AGT fusion protein using the label L.

12. A method for detecting a protein, wherein the protein is incorporated into an $O^6$ alkyl guanine DNA alkyltransferase (AGT) fusion protein, the AGT fusion protein is contacted with a compound of formula (I) according to claim 1, and the AGT fusion protein is detected using the label L.

13. The method of claim 12 wherein the AGT fusion protein is contacted with a compound of formula (I) in vitro.

14. The method of claim 12 wherein the AGT fusion protein is contacted with a compound of formula (I) in vivo or in cell culture.

\* \* \* \* \*